(12) United States Patent
Govari et al.

(10) Patent No.: US 11,957,442 B2
(45) Date of Patent: Apr. 16, 2024

(54) CEREBROSPINAL-FLUID-PRESSURE-MEASURING DEVICE

(71) Applicant: Biosense Webster (Israel) Ltd., Yokneam (IL)

(72) Inventors: Assaf Govari, Haifa (IL); Ilya Sitnitsky, Nahariya (IL); Yehuda Algawi, Binyamina (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 597 days.

(21) Appl. No.: 16/591,912

(22) Filed: Oct. 3, 2019

(65) Prior Publication Data
US 2021/0100464 A1    Apr. 8, 2021

(51) Int. Cl.
*A61B 5/03*      (2006.01)
*A61B 5/00*      (2006.01)

(52) U.S. Cl.
CPC ............ *A61B 5/032* (2013.01); *A61B 5/6864* (2013.01); *A61B 2562/0247* (2013.01)

(58) Field of Classification Search
None
See application file for complete search history.

(56) References Cited

U.S. PATENT DOCUMENTS

| | | | |
|---|---|---|---|
| 4,062,354 A * | 12/1977 | Taylor | G01L 9/105 600/561 |
| 4,265,252 A | 5/1981 | Chubbuck et al. | |
| 4,572,212 A * | 2/1986 | Letterio | A61B 5/031 606/1 |
| 4,593,703 A | 6/1986 | Cosman | |
| 6,432,058 B1 * | 8/2002 | Sloth | A61B 5/417 600/461 |

(Continued)

FOREIGN PATENT DOCUMENTS

DE     35 20 833 A1    12/1986

OTHER PUBLICATIONS

EP 20199773.1-1001—Extended European Search Report dated Mar. 10, 2021.

(Continued)

*Primary Examiner* — Benjamin S Melhus
*Assistant Examiner* — Samuel C Kim
(74) *Attorney, Agent, or Firm* — Troutman Pepper Hamilton Sanders LLP (57) ABSTRACT

A cerebrospinal-fluid-pressure-measuring device including a pressure gauge including a hollow cylindrical body for inserting through a skull and having a lower and upper end, and an inner surface, a membrane attached to the lower end and to move under a pressure of cerebrospinal fluid within the skull, and coils including a stationary coil disposed in the cylindrical body and connected to the inner surface so as to remain stationary, and a moving coil disposed in the cylindrical body and connected to the membrane so that the moving coil moves when the membrane moves under the pressure, one of the coils being configured as a transmitting coil and another of the coils being configured as a receiving coil, and a control unit to apply an input signal to the transmitting coil and receive an output signal from the receiving coil, and to generate an indication of the pressure.

29 Claims, 4 Drawing Sheets

(56) References Cited

U.S. PATENT DOCUMENTS

| | | | |
|---|---|---|---|
| 6,926,670 B2* | 8/2005 | Rich | A61B 5/6882 600/459 |
| 2006/0020224 A1 | 1/2006 | Geiger | |
| 2006/0025704 A1 | 2/2006 | Stendel et al. | |
| 2008/0139959 A1 | 6/2008 | Miethke et al. | |
| 2009/0143696 A1* | 6/2009 | Najafi | A61B 5/6864 600/561 |
| 2010/0058583 A1* | 3/2010 | Cros | A61B 5/02055 257/E21.09 |
| 2010/0298895 A1* | 11/2010 | Ghaffari | A61B 5/14546 607/116 |
| 2011/0066072 A1 | 3/2011 | Kawoss et al. | |
| 2011/0160560 A1 | 6/2011 | Stone | |
| 2012/0265028 A1* | 10/2012 | Hughes | A61B 5/1117 600/301 |
| 2014/0276180 A1* | 9/2014 | Dextradeur | A61B 5/6864 600/544 |
| 2014/0378783 A1* | 12/2014 | Ledet | A61B 5/14546 600/587 |
| 2015/0119752 A1 | 4/2015 | Seaver et al. | |

OTHER PUBLICATIONS

Communication pursuant to Article 94(3) EPC issued in European Patent Application No. 20 199 773.1 dated May 24, 2022.

* cited by examiner

FIG. 1

FIG. 2B
Section A-A

CEREBROSPINAL-FLUID-PRESSURE-MEASURING DEVICE

FIELD OF THE INVENTION

The present invention relates to a pressure-measuring device, and in particular, but not exclusively to, a cerebrospinal-fluid-pressure-measuring device.

BACKGROUND

There are a number of situations, including in emergency units and trauma and hydrocephalous cases, where it is important to measure the pressure of the cerebrospinal fluid (CSF) in the skull of a patient. Present systems typically use a pressure gauge which is inserted through the skull, but these are relatively large and unwieldly, and inserting them through the skull is time consuming.

U.S. Pat. No. 4,593,703 to Cosman describes an implantable telemetric differential pressure sensing device. The implanted device includes a planar, closed, conductive loop which moves with a flexible diaphragm, the diaphragm moving upon changes in the difference of two bodily pressures on its opposite sides. The position of the conductive loop relative to a resonant circuit fixed in the device determines the resonant frequency of the resonant circuit. The resonant frequency is detected telemetrically outside the body, and its value is used to determine the difference in the two bodily pressures.

US Published Patent Application 2011/0066072 of Kawoos, et al., describes an intracranial pressure device for measuring CSF pressure in a skull including a housing located between the scalp and the skull containing pressure device circuitry and a conduit extending downward from the housing to the vicinity of the CSF. A pressure sensor is coupled to the conduit and located in communication with the CSF wherein the pressure sensor directly senses the pressure of the CSF and provides a signal representative of the pressure of the CSF to the pressure device circuitry by way of the conduit. The skull has a dura and the conduit extends by way of an opening through the skull and an opening through the dura to position the sensor in direct contact with the CSF. A fluid reservoir can be in communication with the CSF by way of a tube and by way of the housing. The fluid reservoir contains CSF.

US Published Patent Application 2006/0020224 of Geiger describes a system and method for monitoring Intracranial pressure (ICP) within a patient on a continuous or periodic basis over an extended period of time. In some situations, a care-giver may want to record ICP measurements over a longer period of time to obtain trend data. A system for monitoring ICP includes a shroud-like, inductive power transmitted element designed to surround at least a substantial portion of a patient's head and power an implanted ICP monitor. The shroud-like element may be a table-mounted device that arcs over the width of the table or bed, providing room for the patient's head.

US Published Patent Application 2015/0119752 of Seaver, et al., describes an implantable subcutaneous device to measure internal body pressure and wirelessly transmit information corresponding to the measured internal body pressure, including a pressure sensor to sense pressure of a particular region of a body of a patient and output a pressure signal corresponding to the sensed pressure, an encoder to receive the pressure signal and encode a signal to produce a sensor information signal to be transmitted to an ex vivo receiver, a transceiver to receive the sensor information signal from the encoder and transmit the sensor information signal to the ex vivo receiver, and a biocompatible housing in which to enclose the pressure sensor, encoder, and transceiver.

U.S. Pat. No. 4,265,252 to Chubbuck, et al., describes an implantable transensor device containing a passive RF resonant circuit having a natural frequency influenced by the pressure of the sensor's environment in a body cavity of a living entity. The circuit of the transensor includes an inductor and a capacitor, at least one of which varies in value in direct relation to variation of environmental pressure to change the resonant frequency of the circuit. The circuit can be externally interrogated to determine the resonant frequency thereof at any point in time by the imposition thereon of swept frequency electromagnetic radiation provided by a monitoring device which determines when some of the radiation is absorbed as a result of the frequency of the radiation being the same as the resonant frequency of the transensor circuit. An imposed relationship exists between the sensed environmental pressure, and the reactance of the reactive components of the circuit. A natural relationship exists between pressure sensitive reactance, and the resonant frequency of the circuit. As a result, an increase in environmental pressure causes a corresponding increase in frequency and a decrease in environmental pressure causes a decrease in frequency.

US Published Patent Application 2008/0139959 of Miethke, et al., describes an implantable device for determining intracranial pressures includes a microchip located in a rigid housing. Pressure transfer through a very thin biocompatible membrane acts on the pressure-measuring device via a transfer medium.

US Published Patent Application 2006/0025704 of Stendel, et al., describes an implantable device for measuring brain parameters. It consists of an electronics unit and a sensor unit integrated therein. The electronics unit is sealed solidly and tightly, it is reusable after its sterilization. The sensor unit comprises at least one single lumen catheter and the sensors arranged therein for pressure and/or temperature measurement.

US Published Patent Application 2011/0160560 of Stone describes an implantable pressure sensor system having a sensor assembly configured and adapted to measure pressure in a volume, the sensor assembly including at least a first MEMS pressure sensor, an application-specific integrated circuit (ASIC) having memory means, temperature compensation system, drift compensation system, and power supply means for powering the sensor assembly, the first MEMS pressure sensor having a pressure sensing element that is responsive to exposed pressure, the pressure sensing element being adapted to generate a pressure sensor signal representative of the exposed pressure, the temperature compensation system being adapted to correct for temperature induced variations in the pressure sensor signal, the drift compensation system being adapted to correct for pressure and temperature induced pressure sensor signal drift.

SUMMARY

There is provided in accordance with an embodiment of the present disclosure, a cerebrospinal-fluid-pressure-measuring device, including a pressure gauge including a hollow cylindrical body configured for inserting through a skull and having a lower end, an upper end, an inner surface, and an outer surface, a membrane attached to the lower end, the membrane being configured to move under a pressure of cerebrospinal fluid within the skull, and a plurality of coils including a stationary coil and a moving coil, the stationary coil being disposed in the hollow cylindrical body and connected to the inner surface of the hollow cylindrical body so as to remain stationary with respect to the hollow cylindrical body, the moving coil being disposed in the hollow cylindrical body and connected to the membrane so that the moving coil moves with respect to the stationary coil when the membrane moves under the pressure from the cerebrospinal fluid, one of the plurality of coils being configured as a transmitting coil and another of the plurality of coils being configured as a receiving coil, and a control unit configured to contact the upper end of the hollow cylindrical body so as to apply an input signal to the transmitting coil and receive an output signal from the receiving coil in response to the input signal, and to generate an indication of the pressure of the cerebrospinal fluid responsively to the output signal.

Further in accordance with an embodiment of the present disclosure the outer surface of the hollow cylindrical body is threaded so as to enable screwing the pressure gauge into the skull for fastening therein.

Still further in accordance with an embodiment of the present disclosure the upper end of the hollow cylindrical body includes a drive or bolt-head to aid screwing the pressure gauge into the skull for fastening therein.

Additionally, in accordance with an embodiment of the present disclosure the moving coil has a first axis and the stationary coil has a second axis, the first axis being substantially parallel to the second axis.

Moreover, in accordance with an embodiment of the present disclosure the first axis is substantially collinear with the second axis.

Further in accordance with an embodiment of the present disclosure a separation of the moving coil and the stationary coil in the direction of the first axis and the second axis is in the range of 0.05 mm to 0.7 mm.

Still further in accordance with an embodiment of the present disclosure the hollow cylindrical body had an outer diameter in the range of 0.5 mm to 3.5 mm.

Additionally, in accordance with an embodiment of the present disclosure the hollow cylindrical body includes a tapered cylinder.

Moreover, in accordance with an embodiment of the present disclosure the lower end of the hollow cylindrical body has an outer diameter in the range of 0.5 mm to 3.2 mm, the upper end of the hollow cylindrical body has an outer diameter in the range of 0.7 mm to 3.5 mm, and the hollow cylindrical body has a length measure from the lower end to the upper end in the range of 3-8 mm long.

Further in accordance with an embodiment of the present disclosure the outer surface of the hollow cylindrical body is threaded so as to enable screwing the pressure gauge into the skull for fastening therein.

Still further in accordance with an embodiment of the present disclosure the upper end of the hollow cylindrical body includes a drive or bolt-head to aid screwing the pressure gauge into the skull for fastening therein.

Additionally, in accordance with an embodiment of the present disclosure the hollow cylindrical body includes a cavity which is hermetically sealed, the cavity including the moving coil disposed therein, the cavity being sealed partially by the membrane.

Moreover, in accordance with an embodiment of the present disclosure the membrane includes a silicone.

Further in accordance with an embodiment of the present disclosure the silicone includes polydimethylsiloxane (PDMS) having a chemical formula of $CH_3[Si(CH_3)_2O]nSi(CH_3)_3$.

Still further in accordance with an embodiment of the present disclosure the control unit is reversibly attachable to the upper end of the hollow cylindrical body.

Additionally, in accordance with an embodiment of the present disclosure the control unit and the upper end include complementary interconnecting features to secure the control unit to the hollow cylindrical body.

Moreover, in accordance with an embodiment of the present disclosure the complementary interconnecting features includes a plurality of electrical connections configured to electrically connect the control unit with the plurality of coils.

Further in accordance with an embodiment of the present disclosure the control unit includes a memory and a processor, which is configured to generate the indication of the pressure of the cerebrospinal fluid and store the indication in the memory.

Still further in accordance with an embodiment of the present disclosure the control unit includes a power supply, and a data interface, which is configured to provide the indication of the pressure stored in the memory to a remote processing device.

There is also provided in accordance with still another embodiment of the present disclosure a pressure gauge device, including a hollow cylindrical body for inserting through a skull and having a lower end, an upper end, an inner surface, and an outer surface, the hollow cylindrical body including a tapered cylinder, a membrane attached to the lower end, the membrane being configured to move under a pressure of cerebrospinal fluid within the skull, the outer surface of the hollow cylindrical body being threaded so as to enable screwing the pressure gauge into the skull for fastening therein, and a plurality of coils including a stationary coil and a moving coil, the stationary coil being disposed in the hollow cylindrical body and connected to the inner surface of the hollow cylindrical body so as to remain stationary with respect to the hollow cylindrical body, the moving coil being disposed in the hollow cylindrical body and connected to the membrane so that the moving coil moves with respect to the stationary coil when the membrane moves under the pressure from the cerebrospinal fluid, one of the plurality of coils being configured as a transmitting coil and another of the plurality of coils being configured as a receiving coil, wherein the upper end of the hollow cylindrical body includes a drive or bolt-head to aid screwing the pressure gauge into the skull for fastening therein, the upper end is configured for interconnecting with a complementary feature of a control unit, which is reversibly attachable to the upper end of the hollow cylindrical body, the upper end includes a plurality of electrical connections configured to electrically connect the control unit with the plurality of coils, the control unit is configured to contact the upper end of the hollow cylindrical body so as to apply an input signal to the transmitting coil and receive an output signal from the receiving coil in response to the input signal, and to generate an indication of the pressure of the cerebrospinal fluid responsively to the output signal.

Additionally, in accordance with an embodiment of the present disclosure the moving coil has a first axis and the stationary coil has a second axis, the first axis being substantially collinear with the second axis.

Moreover, in accordance with an embodiment of the present disclosure the membrane includes a silicone.

Further in accordance with an embodiment of the present disclosure the silicone includes polydimethylsiloxane (PDMS) having a chemical formula of $CH_3[Si(CH_3)_2O]nSi(CH_3)_3$.

There is also provided in accordance with still another embodiment of the present disclosure a method of use of a cerebrospinal-fluid-pressure-measuring device, the method including inserting a hollow cylindrical body of a pressure gauge through a skull, the hollow cylindrical body having a lower end, an upper end, an inner surface, and an outer surface, the pressure gauge also including a membrane attached to the lower end, the membrane being configured to move under a pressure of cerebrospinal fluid within the skull, and a plurality of coils including a stationary coil and a moving coil, the stationary coil being disposed in the hollow cylindrical body and connected to the inner surface of the hollow cylindrical body so as to remain stationary with respect to the hollow cylindrical body, the moving coil being disposed in the hollow cylindrical body and connected to the membrane so that the moving coil moves with respect to the stationary coil when the membrane moves under the pressure from the cerebrospinal fluid, one of the plurality of coils being configured as a transmitting coil and another of the plurality of coils being configured as a receiving coil, attaching a control unit to the upper end of the hollow cylindrical body, applying an input signal to the transmitting coil, receiving an output signal from the receiving coil in response to the input signal, and generating an indication of the pressure of the cerebrospinal fluid responsively to the output signal.

Still further in accordance with an embodiment of the present disclosure the outer surface of the hollow cylindrical body is threaded, the method further including screwing the pressure gauge into the skull for fastening therein.

Additionally, in accordance with an embodiment of the present disclosure the upper end of the hollow cylindrical body includes a drive or a bolt-head, the method further including screwing the pressure gauge into the skull for fastening therein.

Moreover, in accordance with an embodiment of the present disclosure the moving coil has a first axis and the stationary coil has a second axis, the first axis being substantially collinear with the second axis.

Further in accordance with an embodiment of the present disclosure the hollow cylindrical body includes a tapered cylinder.

Still further in accordance with an embodiment of the present disclosure the membrane includes a silicone.

Additionally, in accordance with an embodiment of the present disclosure the silicone includes polydimethylsiloxane (PDMS) having a chemical formula of $CH_3[Si(CH_3)_2O]nSi(CH_3)_3$.

BRIEF DESCRIPTION OF THE DRAWINGS

The present invention will be understood from the following detailed description, taken in conjunction with the drawings in which.

DESCRIPTION OF EXAMPLE EMBODIMENTS

Overview

By way of introduction, installing a pressure gauge into the skull to measure cerebrospinal fluid (CSF) pressure may involve many challenges, including the time taken to insert the gauge through the skull and securing the pressure gauge once inserted. A large and unwieldy gauge apart from being difficult to handle, may also be uncomfortable for the patient. Additionally, an undesirable result of using a large gauge is that a large hole may need to be made into the skull. Although, producing smaller pressure gauges may alleviate some of the above challenges, smaller pressure gauges still need to maintain sensing accuracy and may also be difficult to handle due to the small size.

Therefore, in some embodiments of the present invention, a cerebrospinal-fluid-pressure-measuring device is provided including a light-weight and compact pressure gauge with a diameter generally in the range of 0.5 mm and 3.5 mm for easy and comfortable insertion through the skull. The outer surface of the pressure gauge may include a screw thread so as to enable screwing the pressure gauge into the skull for fastening therein. Once the pressure gauge has been inserted through the skull, a control unit may be attached to the upper end of the pressure gauge. The control unit may power the pressure gauge, acquire readings from the pressure gauge, and provide an indication of the pressure to a remote processing device.

The pressure gauge includes a coil and membrane arrangement, described in more detail below, to provide accurate pressure readings so that sensing accuracy is not compromised in the light-weight and compact pressure gauge. The pressure gauge generally comprises biocompatible materials where contact with the skull and the CSF are likely to occur.

For additional ease of insertion, the upper end of the hollow cylindrical body optionally includes a drive in which to reversibly insert a screwdriving device or tool to aid screwing the pressure gauge into the skull for fastening therein. The drive is optionally formed so that it interconnects with a complementary feature of the control unit, which is reversibly attachable to the upper end of the hollow cylindrical body. In other exemplary embodiments, the upper end of the hollow cylindrical body optionally includes a bolt-head for engaging a wrench to aid screwing the pressure gauge into the skull for fastening therein.

In some exemplary embodiments, the pressure gauge may be formed as a tapered cylinder for ease of insertion through the skull. To illustrate the compactness of the pressure gauge, the tapered cylinder may have an outer diameter at its lower end (inserted closest to the CSF) of generally between 0.5 mm and 3.2 mm (for example 1.2 mm) and an outer diameter at its upper end (generally remaining outside the skull) of generally between 0.7 mm and 3.5 mm (for example 1.7 mm). The pressure gauge may generally have a length-measure from its lower end to its upper end in the range of 3-8 mm (for example 4-5 mm).

A membrane is attached to the lower end of the cylindrical body so that when the pressure gauge is inserted through the skull the membrane moves under the pressure of the CSF within the skull. The membrane may include a silicone or other flexible biocompatible material. The silicone may include polydimethylsiloxane (PDMS) having a chemical formula of $CH_3[Si(CH_3)_2O]nSi(CH_3)_3$.

A plurality of coils including a stationary coil and a moving coil are disposed in the cylindrical body. The coils are generally disposed in the cylindrical body so that their axes are collinear with the axis of the cylindrical body. However, other arrangements of the coils with respect to each other and the cylindrical body are possible. The stationary coil is connected to the inner surface of the cylindrical body so as to remain stationary with respect to the hollow cylindrical body even when the membrane moves under pressure of the CSF. The moving coil, on the other hand, is connected to the membrane so that the moving coil moves with respect to the stationary coil when the membrane moves under the pressure from the CSF.

The upper end of the cylindrical body generally includes electrical connections configured to electrically connect the control unit with the coils disposed in the pressure gauge. One of the coils is designated as a transmitting coil and the other coil is designated as a receiving coil. The designation of which coil is the receiving coil or the transmitting coil is generally arbitrary. The control unit applies an input signal to the transmitting coil and receives an output signal from the receiving coil in response to the input signal. As the distance between the two coils changes according to the pressure exerted on the membrane, this change is directly related to the output signal generated at the receiving coil. The control unit may generate an indication of the pressure of the CSF responsively to the output signal. The control unit may need to be calibrated to provide a correspondence between the output signal and respective pressure values.

System Description

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.

Figure 1:
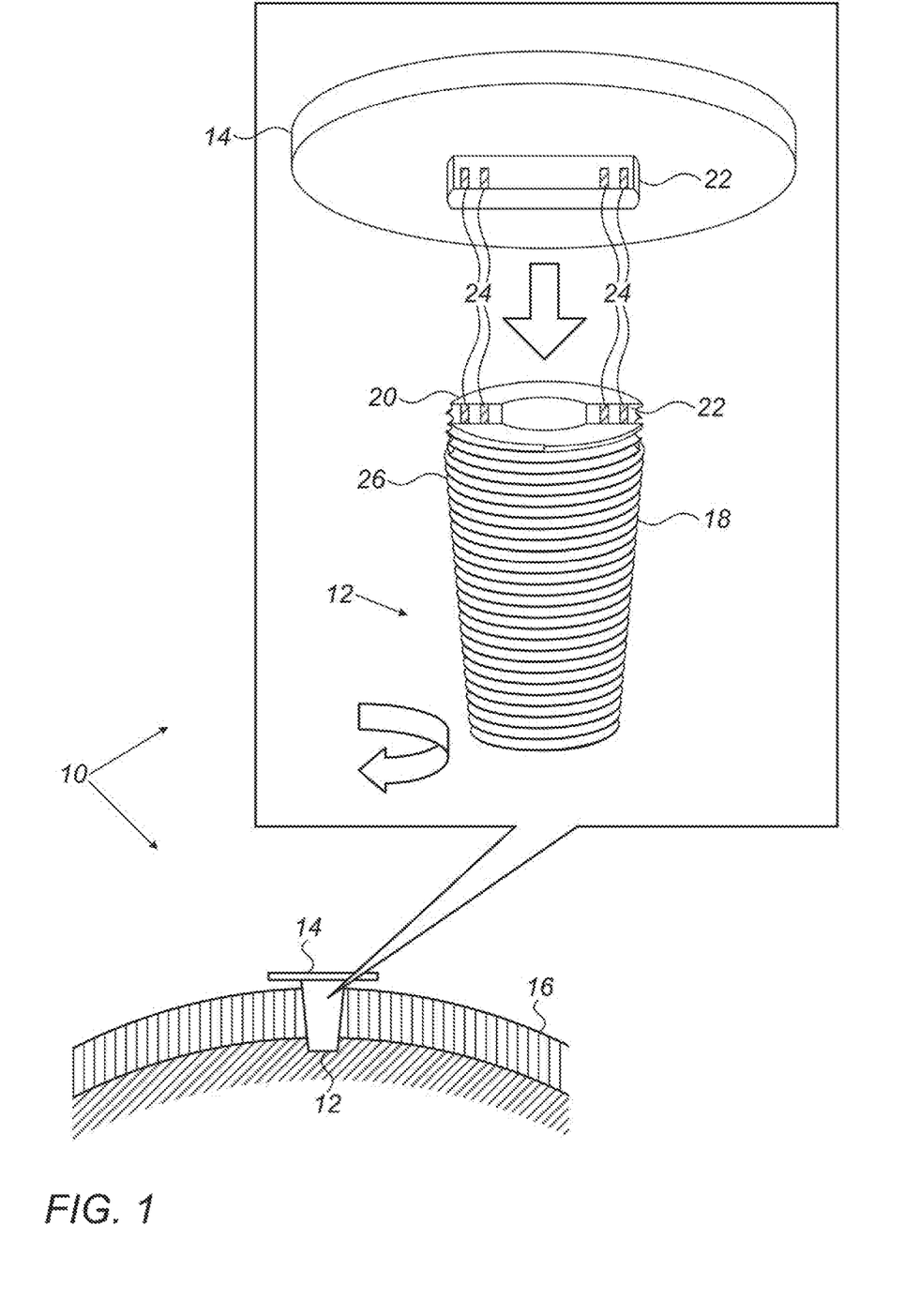
FIG. 1 is a schematic pictorial view of a cerebrospinal-fluid-pressure-measuring device constructed and operative in accordance with an embodiment of the present invention.

Reference is now made to FIG. 1, which is a schematic pictorial view of a cerebrospinal-fluid-pressure-measuring device 10 constructed and operative in accordance with an exemplary embodiment of the present invention. The cerebrospinal-fluid-pressure-measuring device 10 includes a pressure gauge 12 and a control unit 14. A hole may be drilled into the skull 16 using any suitable drilling instrument for this purpose. The pressure gauge 12 includes a hollow cylindrical body 18 is configured for inserting through a skull 16. The hollow cylindrical body 18 is described in more detail with reference to FIGS. 2A and 2B. The hollow cylindrical body 18 may include a screw thread on its outer surface 26 to aid insertion and securing the pressure gauge 12 in the skull 16.

The control unit 14 is configured to contact an upper end 20 of the hollow cylindrical body 18 so as to apply an input signal to a coil disposed in the hollow cylindrical body 18 and receive an output signal from another coil disposed in the hollow cylindrical body 18. The coils are not shown in FIG. 1, but are shown and described in more detail with reference to FIGS. 2A and 2B. The control unit 14 is configured to generate an indication of pressure of the CSF in the skull 16 responsively to the output signal. The control unit is described in more detail with reference to FIGS. 3 and 4.

The control unit 14 is configured to be reversibly attachable to the upper end 20 of the hollow cylindrical body 18. In alternative exemplary embodiments the control unit 14 may be permanently fixed to the pressure gauge 12.

The control unit 14 and the upper end 20 of the hollow cylindrical body 18 include complementary interconnecting features 22 to secure the control unit 14 to the hollow cylindrical body 18. The interconnecting features 22 may be configured to provide a pressure fit or an interlocking mechanism, by way of example only. In some exemplary embodiments, the control unit 14 may be screwed to the skull 16 in one or more locations. Additionally, or alternatively, the control unit 14 may be affixed to the skull 16 using a suitable adhesive. Securing the control unit 14 to the skull 16 is particularly useful when the outer surface of the hollow cylindrical body 18 is not threaded. Even when the hollow cylindrical body 18 is threaded, the control unit 14 may be secured to the skull 16 to provide extra adhesion.

The control unit 14 and the pressure gauge 12 generally include a plurality of electrical connections 24 to electrically connect the control unit 14 and the pressure gauge 12. The electrical connections 24 are generally disposed on the interconnecting features 22 of the pressure gauge 12 and the control unit 14.

Figure 2A:
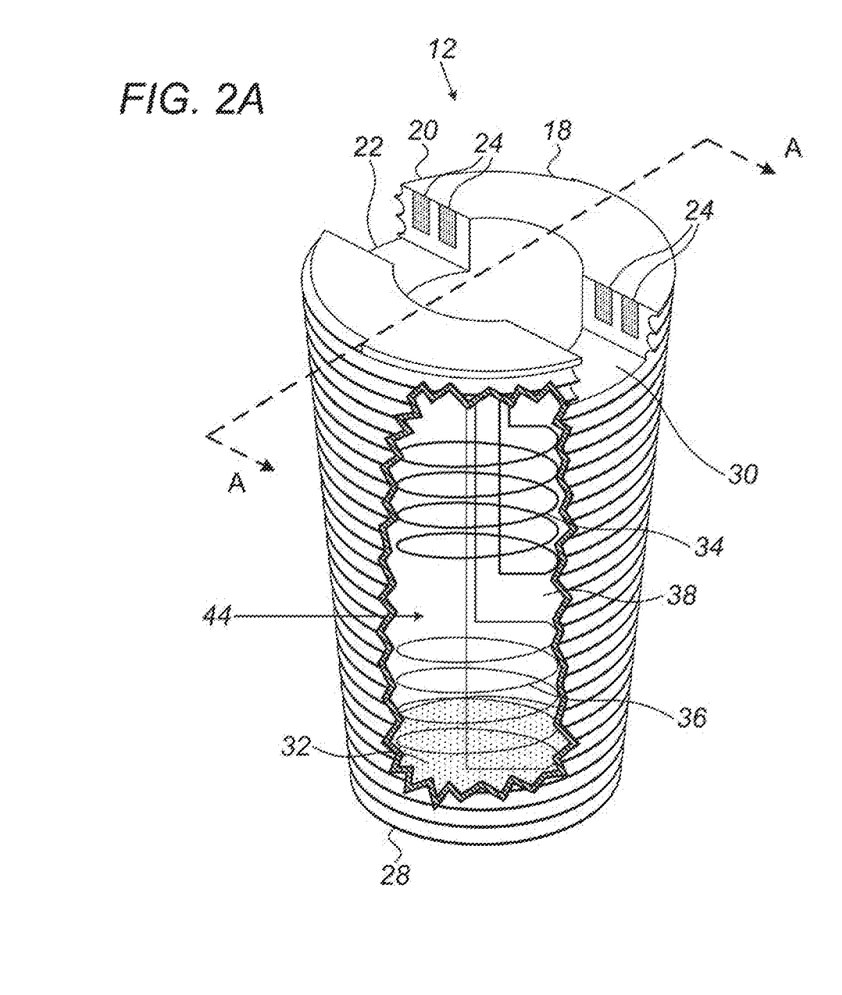
FIG. 2A is an orthogonal cutaway view of a pressure gauge of the cerebrospinal-fluid-pressure-measuring device of FIG. 1 constructed and operative in accordance with an embodiment of the present invention.
Figure 2B:
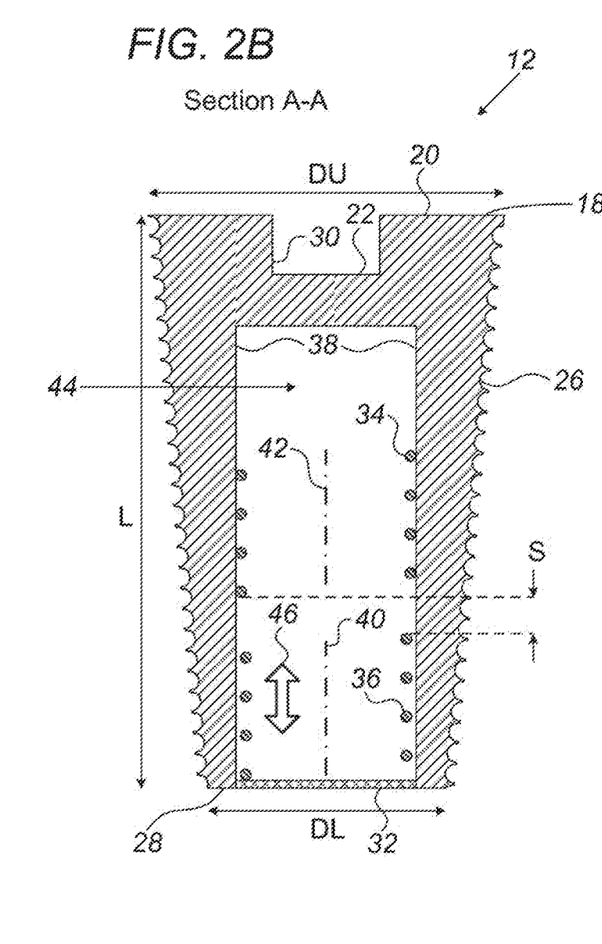
FIG. 2B is a longitudinal cross-sectional view of the pressure gauge of FIG. 2A along line A-A.

Reference is now made to FIGS. 2A-2B. FIG. 2A is an orthogonal cutaway view of the pressure gauge 12 of the cerebrospinal-fluid-pressure-measuring device 10 of FIG. 1 constructed and operative in accordance with an exemplary embodiment of the present invention. FIG. 2B is a longitudinal cross-sectional view of the pressure gauge 12 along line A-A of FIG. 2A.

The hollow cylindrical body 18 may include a tapered cylinder. In some exemplary embodiments, the hollow cylindrical body 18 is not tapered. The hollow cylindrical body 18 may be made of any suitably durable material. The outer surface 26 of the hollow cylindrical body 18 generally comprises a biocompatible material, for example, but not limited to, titanium or stainless steel.

An outer diameter of the hollow cylindrical body 18 is generally, but not exclusively, in the range of 0.5 mm to 3.5 mm, but smaller or larger diameters may also be implemented. When the hollow cylindrical body 18 is tapered, a lower end 28 of the hollow cylindrical body 18 may have an outer diameter (DL) generally, but not exclusively, in the range of 0.5 mm to 3.2 mm, for example, 1.2 mm, but smaller or larger diameters may also be implemented, and the upper end 20 of the hollow cylindrical body 18 may have an outer diameter (DU) generally, but not exclusively, in the range of 0.7 mm to 3.5 mm, for example, 1.7 mm, but smaller or larger diameters may also be implemented. The hollow cylindrical body 18 may have a length measure (L) (height) from the lower end 28 to the upper end 20 generally, but not exclusively, in the range of 3-8 mm, for example 4-5 mm long, but smaller or larger lengths may also be implemented. The diameter of the hole drilled in the skull is generally, but not exclusively, equal to or greater than the diameter of the lower end 28. For example, if the diameter of the lower end 28 is 1.2 mm and the diameter of the upper end 20 is 1.7 mm, the diameter of the hole drilled may be in the range of 1.2 mm to 1.6 mm.

The outer surface 26 of the hollow cylindrical body 18 is threaded so as to enable screwing the pressure gauge 12 into the skull 16 (FIG. 1) for easier fastening therein. The upper end 20 of the hollow cylindrical body 18 may include a drive 30 in which to reversibly insert a screwdriving tool to aid screwing the pressure gauge 12 into the skull 16 for fastening therein.

The hollow cylindrical body 18 includes a membrane 32 attached to the lower end 28 of the hollow cylindrical body 18 using any suitable adhesive, by way of example only. The membrane 32 is configured to move under the pressure of the CSF within the skull 16. The membrane may include any suitable flexible biocompatible material. It has been determined that a silicone-based material is suitable for the membrane 32. The silicone may include polydimethylsiloxane (PDMS) having a chemical formula of $CH_3[Si(CH_3)_2O]nSi(CH_3)_3$, similar to that used in the shell of breast implants.

The pressure gauge 12 includes a plurality of coils including a stationary coil 34 and a moving coil 36, disposed in the hollow cylindrical body 18. The stationary coil 34 is connected to an inner surface 38 of the hollow cylindrical body 18 so as to remain stationary with respect to the hollow cylindrical body 18. One end of the moving coil 36 is connected to the membrane 32 so that the moving coil 36 moves (arrow 46) with respect to the stationary coil 34 when the membrane 32 moves under the pressure from the CSF. The expected displacement of the coil 36 is generally, but not exclusively, within the range of 0.05 mm to 0.5 mm. Depending on the implementation, the smallest displacements that are measured may be around 0.01 mm. The moving coil 36 has an axis 40 and the stationary coil 34 has an axis 42. The axis 40 and the axis 42 are substantially parallel to each other. Although the axis 40 and the axis 42 are generally aligned with each other, the term "substantially parallel" used in the specification and claims is defined to include the axes 40, 42 not being completely parallel but being within 30 degrees of each other. In the exemplary embodiment shown in FIGS. 2A and 2B the axes 40, 42 are substantially collinear. Although the axis 40 and the axis 42 are generally aligned, the term "substantially collinear" used in the specification and claims is defined to include the axes 40, 42 not being completely collinear or even completely parallel but separated up to a distance of a third of the average diameter of the coils 34, 36 and being within 30 degrees of each other.

The separation S of the moving coil 36 and the stationary coil 34 in the direction of the axes 40, 42 is generally, but not exclusively, in the range of 0.05 mm to 0.7 mm, for example 0.1 mm. The stationary coil 34 and the moving coil 36 need to be separated enough to allow for full movement of the moving coil 36 under pressure of the CSF while being close enough together so that a signal emitted by one of the coils is received by the other coil and has a large enough amplitude to provide meaningful pressure readings. The thickness of the wire of the coils 34, 36 may be any suitable thickness and the coils may have any suitable number of winds. In one exemplary embodiment, the thickness of the wire of the coils is between 0.01-0.05 mm with between 10 to 30 winds per coil.

The stationary coil 34 and the moving coil 36 are connected to the electrical connections 24 disposed in the upper end 20 of the hollow cylindrical body 18. One of the coils 34, 36 is configured as a transmitting coil and another of the coils 34, 36 is configured as a receiving coil. The coils 34, 36 may be configured as the transmitting coil or the receiving coil by the wiring of the coils 34, 36 and the control unit 14 with respect to the electrical connections 24 and/or by the control unit 14 selecting which of the coils 34, 36 should be the transmitting coil and the receiving coil.

The hollow cylindrical body 18 includes a cavity 44 which is hermetically sealed. The cavity 44 includes the stationary coil 34 and the moving coil 36 disposed therein. The cavity 44 is sealed by the membrane 32, the inner surface 38, and the upper end 20 of the hollow cylindrical body 18. The pressure in the cavity is generally set to equal about 1 Atmosphere, but may be set to any suitable value.

Figure 3:
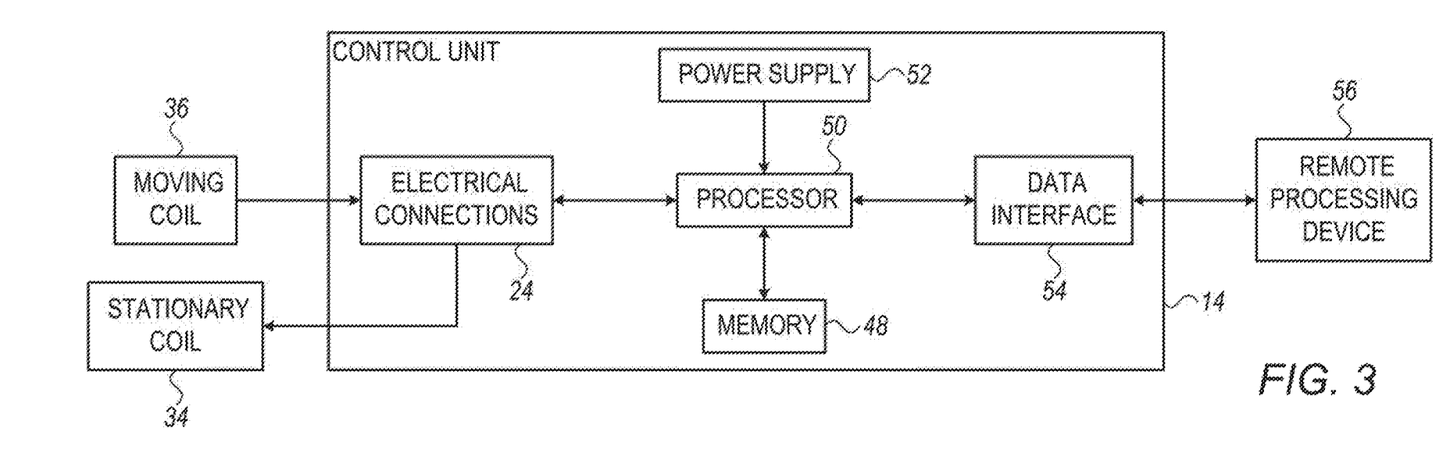
FIG. 3 is a block diagram view of a control unit of the cerebrospinal-fluid-pressure-measuring device of FIG. 1 constructed and operative in accordance with an embodiment of the present invention.

Reference is now made to FIG. 3, which is a block diagram view of the control unit 14 of the cerebrospinal-fluid-pressure-measuring device 10 of FIG. 1 constructed and operative in accordance with an exemplary embodiment of the present invention. The control unit 14 may include a memory 48, a processor 50, a power supply 52, a data interface 54 and the electrical connections 24. The different elements of the control unit 14 receive power from the power supply 52. The memory 48 is configured to store data (and software) used by the processor 50 as well as pressure data described in more detail below. The memory 48 may comprise volatile and/or non-volatile memory. The data interface 54 is configured to transfer data to (and from) a remote processing device 56. The data interface 54 may transfer data using any suitable protocol, for example, but not limited to, a wireless (WIFI® or Bluetooth®) and/or a wired data transfer protocol.

The control unit 14 is configured to contact the upper end 20 (FIGS. 2A-2B) of the hollow cylindrical body 18 (FIGS. 2A-2B) so as to apply an input signal to the transmitting coil (e.g., the stationary coil 34) and receive an output signal from the receiving coil (e.g., the moving coil 36) in response to the input signal. As the distance between the two coils 34, 36 changes according to the pressure exerted on the membrane 32 (FIGS. 2A-2B), the change in distance is directly related to the output signal generated at the receiving coil. The processor 50 is configured to generate an indication of the pressure of the CSF responsively to the output signal. In one exemplary embodiment pressure values of between 5-50 mmHg are expected with an accuracy of about 0.01 mmHg. The control unit 14 may be calibrated based on a plurality of measurements of the output signal at known CSF pressures measured by a calibrated device.

Figure 4:
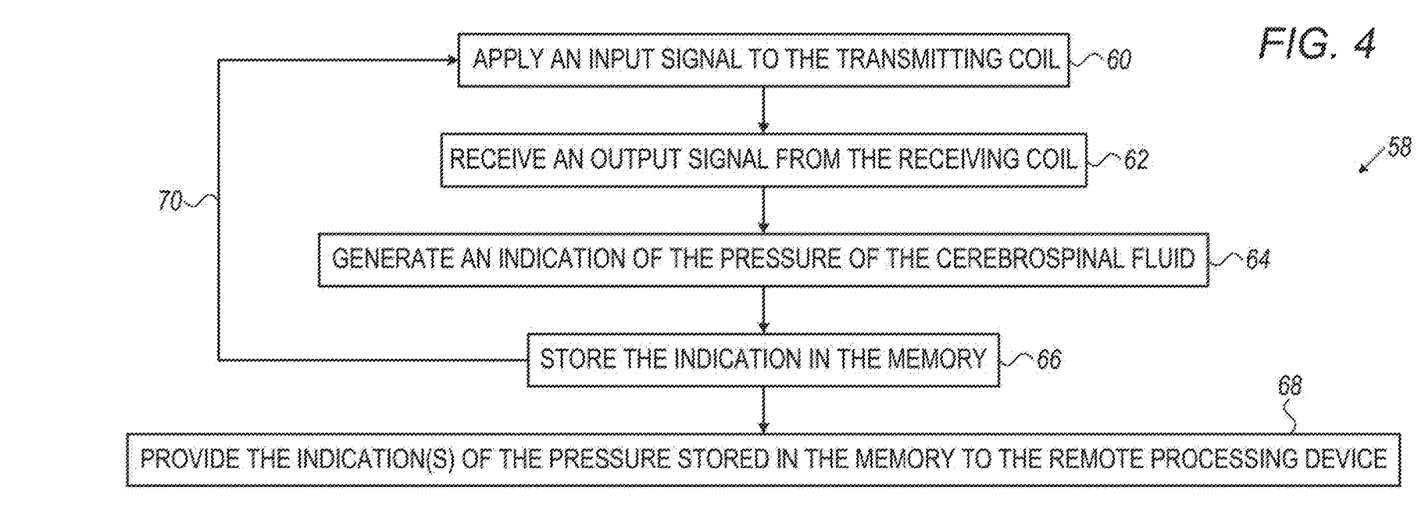
FIG. 4 is a flow diagram including exemplary steps in a method of operation of the control unit of FIG. 3.

In some exemplary embodiments, the control unit 14 may include the electrical connections 24 and the data interface 54 to the remote processing device 56 without including the memory 48, the processor 50 and the power supply 52 wherein the functionality of the processor 50 described with reference to FIG. 4 is provided by the remote processing device 56. In other exemplary embodiments, the control unit 14 may include the electrical connections 24, the data interface 54, the processor 50 and the memory 48, but power is supplied by an external power supply, for example, in the remote processing device 56, via a suitable connection, e.g., USB cable or wireless power.

Reference is now made to FIG. 4, which is a flow diagram 58 including exemplary steps in a method of operation of the control unit 14 of FIG. 3. Reference is also made to FIG. 3. The processor 50 is configured to generate the input signal and apply (block 60) the input signal to the transmitting coil via the relevant electric connections 24. The processor 50 is configured to receive (block 62) the output signal from the receiving coil in response to the input signal. The processor 50 is also configured to generate (block 64) the indication of the pressure of the CSF responsively to the output signal and store (block 66) the indication in the memory 48. The indication stored in memory may be the output signal or a value calculated by the processor 50 and based on the output signal, for example, but not limited to a pressure value in a suitable unit of pressure. The indication may also be stored with a time stamp indicating the time at which the indication of pressure was measured. The above steps of blocks 60-68 may be repeated (arrow 70) periodically providing a plurality of pressure readings. The processor 50 is configured to provide the indication(s) of the pressure stored in the memory 48 to the remote processing device 56 via the data interface 54.

In practice, some or all of the functions of the processor 50 may be combined in a single physical component or, alternatively, implemented using multiple physical components. These physical components may comprise hard-wired or programmable devices, or a combination of the two. In some embodiments, at least some of the functions of the processing circuitry may be carried out by a programmable processor under the control of suitable software. This software may be downloaded to the control unit 14 in electronic form, over a network, for example. Alternatively, or additionally, the software may be stored in tangible, non-transitory computer-readable storage media.

Figure 5A:
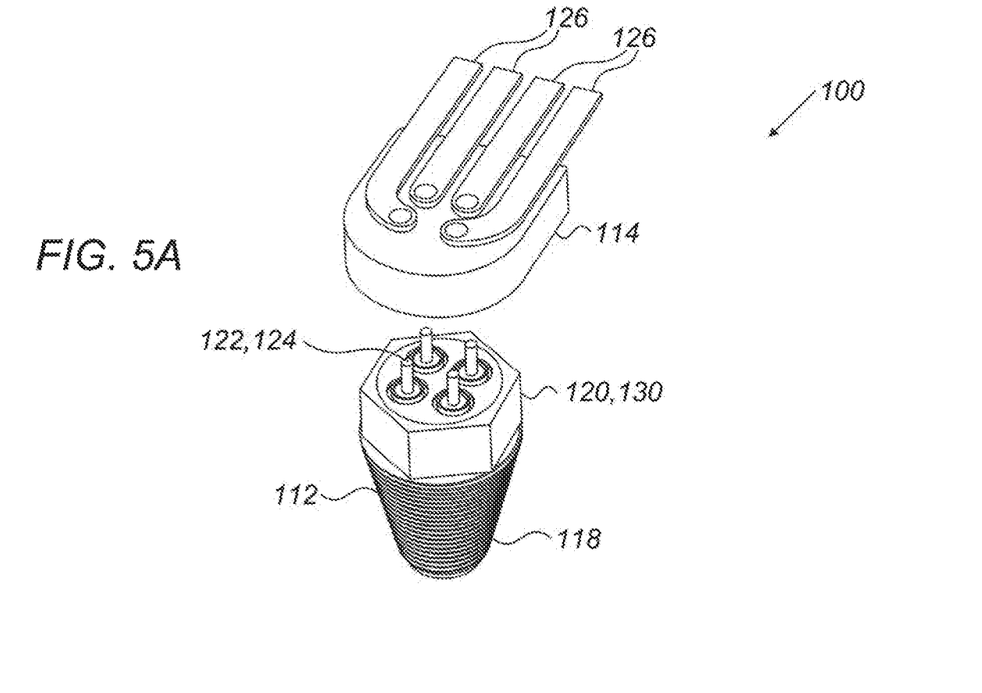
FIGS. 5A and 5B are schematic pictorial views of the cerebrospinal-fluid-pressure-measuring device constructed and operative in accordance with an alternative embodiment of the present invention.
Figure 5B:
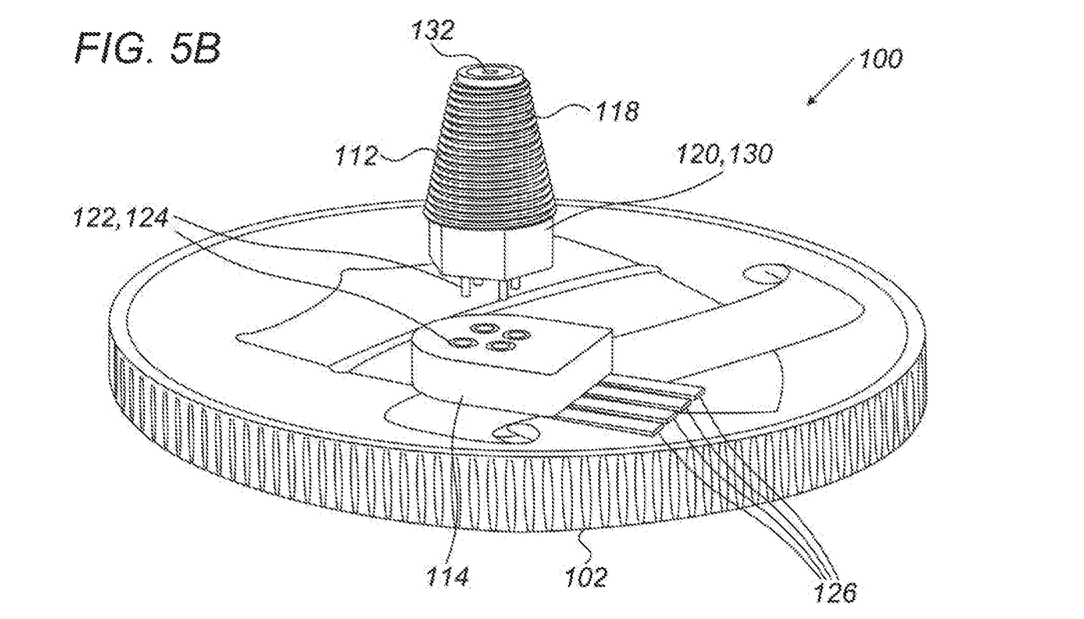

Reference is now made to FIGS. 5A and 5B, which are schematic pictorial views of a cerebrospinal-fluid-pressure-measuring device 100 constructed and operative in accordance with an alternative exemplary embodiment of the present invention. FIG. 5B shows the cerebrospinal-fluid-pressure-measuring device 100 disposed on a one cent piece 102 to emphasize the compactness of the cerebrospinal-fluid-pressure-measuring device 100. The cerebrospinal-fluid-pressure-measuring device 100 of FIGS. 5A and 5B includes a pressure gauge 112 (with a hollow cylindrical body 118 and a membrane 132) and a control unit 114. The cerebrospinal-fluid-pressure-measuring device 100 is substantially the same as the cerebrospinal-fluid-pressure-measuring device 10 described above with reference to FIGS. 1-4 except for the following differences. The shape of an upper end 120 of the hollow cylindrical body 118 is configured as a bolt head 130, e.g., a hexagonal-shaped bolt-head, so as to insert the hollow cylindrical body 118 through the skull using a wrench or similar tool. The pressure gauge 112 and the control unit 114 include interconnecting features 122 and electrical connections 124 configured as prongs and sockets providing physical and electrical interconnection between the pressure gauge 112 and the control unit 114. The interconnecting features 122 may provide a pressure fit or may include other features to allow clicking the pressure gauge 112 and the control unit 114 together. The control unit 14 includes a plurality of other electrical connections 126 for connection to a remote processing device.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and subcombinations of the various features described hereinabove, as well as variations and modifications thereof which would occur to persons skilled in the art upon reading the foregoing description and which are not disclosed in the prior art.

What is claimed is:

1. A cerebrospinal-fluid-pressure-measuring device, comprising:
 a pressure gauge including:
  a hollow cylindrical body configured for inserting through a skull and having a lower end, an upper end, a length measure from the lower end to the upper end extending in a length direction, an inner surface extending along the length direction of the hollow cylindrical body, an outer surface, and a cavity defined by the inner surface from the lower end towards the upper end, wherein the upper end of the hollow cylindrical body includes a drive or bolt head to aid in screwing the pressure gauge into the skull for fastening therein;
  a membrane attached to the lower end so as to at least partially seal the cavity, the membrane being configured to move under a pressure of cerebrospinal fluid within the skull; and
  a plurality of coils including a stationary coil and a moving coil, the stationary coil being (i) disposed in the cavity of the hollow cylindrical body, (ii) connected to the inner surface of the hollow cylindrical body so as to remain stationary with respect to the hollow cylindrical body, and (iii) extending along the length direction along the inner surface, the moving coil being disposed in the cavity of the hollow cylindrical body, extending along the inner surface, and directly connected to the membrane so that the moving coil moves with respect to the stationary coil when the membrane moves under the pressure from the cerebrospinal fluid, one of the stationary coil or the moving coil being configured as a transmitting coil and another of the stationary coil or the moving coil being configured as a receiving coil; and
 a control unit comprising a memory and a processor configured to contact the upper end of the hollow cylindrical body so as to apply an input signal to the transmitting coil and receive an output signal from the receiving coil in response to the input signal, and to generate an indication of the pressure of the cerebrospinal fluid responsively to the output signal.

2. The device according to claim 1, wherein the outer surface of the hollow cylindrical body is threaded so as to enable screwing the pressure gauge into the skull for fastening therein.

3. The device according to claim 1, wherein the moving coil has a first axis and the stationary coil has a second axis, the first axis being substantially parallel to the second axis.

4. The device according to claim 3, wherein the first axis is substantially collinear with the second axis.

5. The device according to claim 4, wherein a separation of the moving coil and the stationary coil in the direction of the first axis and the second axis is in the range of 0.05 mm to 0.7 mm.

6. The device according to claim 1, wherein the hollow cylindrical body had an outer diameter in the range of 0.5 mm to 3.5 mm.

7. The device according to claim 1, wherein the hollow cylindrical body includes a tapered cylinder.

8. The device according to claim 7, wherein: the lower end of the hollow cylindrical body has an outer diameter in the range of 0.5 mm to 3.2 mm; the upper end of the hollow cylindrical body has an outer diameter in the range of 0.7 mm to 3.5 mm; and the hollow cylindrical body has a length measure from the lower end to the upper end in the range of 3-8 mm long.

9. The device according to claim 7, wherein the outer surface of the hollow cylindrical body is threaded so as to enable screwing the pressure gauge into the skull for fastening therein.

10. The device according to claim 1, wherein the cavity is hermetically sealed.

11. The device according to claim 1, wherein the membrane includes a silicone.

12. The device according to claim 11, wherein the silicone includes polydimethylsiloxane (PDMS) having a chemical formula of $CH_3[Si(CH_3)_2O]_nSi(CH_3)_3$.

13. The device according to claim 1, wherein the control unit is reversibly attachable to the upper end of the hollow cylindrical body.

14. The device according to claim 13, wherein the control unit and the upper end include complementary interconnecting features to secure the control unit to the hollow cylindrical body.

15. The device according to claim 14, wherein the complementary interconnecting features includes a plurality of electrical connections configured to electrically connect the control unit with the plurality of coils.

16. The device according to claim 15, wherein the control unit is configured to generate the indication of the pressure of the cerebrospinal fluid and store the indication in the memory.

17. The device according to claim 16, wherein the control unit includes a power supply, and a data interface, which is configured to provide the indication of the pressure stored in the memory to a remote processing device.

18. The device according to claim 1, wherein the transmitting coil and the receiving coil each have between 10 and 30 winds per coil.

19. The device according to claim 1, wherein the transmitting coil and the receiving coil each are made from wire with a thickness in the range of 0.01 mm to 0.05 mm.

20. A pressure gauge device, comprising:
a hollow cylindrical body for inserting through a skull and having a lower end, a length measure from the lower end to the upper end extending in a length direction, an upper end, an inner surface extending along the length direction of the hollow cylindrical body, an outer surface, and a cavity defined by the inner surface from the lower end towards the upper end, the hollow cylindrical body including a tapered cylinder, wherein the upper end of the hollow cylindrical body includes a drive or bolt head to aid in screwing the pressure gauge device into the skull for fastening therein;
a membrane attached to the lower end so as to at least partially seal the cavity, the membrane being configured to move under a pressure of cerebrospinal fluid within the skull, the outer surface of the hollow cylindrical body being threaded so as to enable screwing the pressure gauge into the skull for fastening therein; and
a plurality of coils including a stationary coil and a moving coil, the stationary coil being (i) disposed in the cavity of the hollow cylindrical body, (ii) connected to the inner surface of the hollow cylindrical body so as to remain stationary with respect to the hollow cylindrical body, and (iii) extending along the length direction along the inner surface, the moving coil being disposed in the cavity of the hollow cylindrical body and directly connected to the membrane so that the moving coil moves with respect to the stationary coil when the membrane moves under the pressure from the cerebrospinal fluid, one of the stationary coil or the moving coil being configured as a transmitting coil and another of the stationary coil or the moving coil being configured as a receiving coil, wherein:
the upper end is configured for interconnecting with a complementary feature of a control unit comprising a memory and a processor, which is reversibly attachable to the upper end of the hollow cylindrical body;
the upper end includes a plurality of electrical connections configured to electrically connect the control unit with the plurality of coils;
the control unit is configured to contact the upper end of the hollow cylindrical body so as to apply an input signal to the transmitting coil and receive an output signal from the receiving coil in response to the input signal, and to generate an indication of the pressure of the cerebrospinal fluid responsively to the output signal.

21. The device according to claim 20, wherein the moving coil has a first axis and the stationary coil has a second axis, the first axis being substantially collinear with the second axis.

22. The device according to claim 20, wherein the membrane includes a silicone.

23. The device according to claim 22, wherein the silicone includes polydimethylsiloxane (PDMS) having a chemical formula of $CH_3[Si(CH_3)_2O]_nSi(CH_3)_3$.

24. A method of use of a pressure gauge, the method comprising:
inserting a hollow cylindrical body of the pressure gauge through a skull, the hollow cylindrical body having a lower end, an upper end, a length measure from the lower end to the upper end extending in a length direction, an inner surface extending along the length direction of the hollow cylindrical body, an outer surface, and a cavity defined by the inner surface from the lower end towards the upper end, wherein the upper end of the hollow cylindrical body includes a drive or bolt head to aid in screwing the pressure gauge into the skull for fastening therein, the pressure gauge also including: a membrane attached to the lower end so as to at least partially seal the cavity, the membrane being configured to move under a pressure of cerebrospinal fluid within the skull; and a plurality of coils including a stationary coil and a moving coil, the stationary coil being (i) disposed in the cavity of the hollow cylindrical body, connected to the inner surface of the hollow cylindrical body so as to remain stationary with respect to the hollow cylindrical body, and (iii) extending along the length direction along the inner surface, the moving coil being disposed in the cavity of the hollow cylindrical body and directly connected to the membrane so that the moving coil moves with respect to the stationary coil when the membrane moves under the pressure from the cerebrospinal fluid, one of the stationary coil or the moving coil being configured as a transmitting coil and another of the stationary coil or the moving coil being configured as a receiving coil;
attaching a control unit to the upper end of the hollow cylindrical body, the control unit comprising a memory and a processor;
applying an input signal to the transmitting coil;
receiving an output signal from the receiving coil in response to the input signal; and
generating an indication of the pressure of the cerebrospinal fluid responsively to the output signal.

25. The method according to claim 24, wherein the outer surface of the hollow cylindrical body is threaded, the method further comprising screwing the pressure gauge into the skull for fastening therein.

26. The method according to claim 24, wherein the moving coil has a first axis and the stationary coil has a second axis, the first axis being substantially collinear with the second axis.

27. The method according to claim 24, wherein the hollow cylindrical body includes a tapered cylinder.

28. The method according to claim 24, wherein the membrane includes a silicone.

29. The method according to claim 28, wherein the silicone includes polydimethylsiloxane (PDMS) having a chemical formula of $CH_3[Si(CH_3)_2O]_nSi(CH_3)_3$.

* * * * *